US00PP34526P2

(12) United States Plant Patent
Dofferhoff et al.

(10) Patent No.: US PP34,526 P2
(45) Date of Patent: Aug. 30, 2022

(54) ***HYDRANGEA* PLANT NAMED 'BEE GREEN'**

(50) Latin Name: *Hydrangea paniculata*
Varietal Denomination: Bee Green

(71) Applicant: Greenwood Investments B.V., Reeuwijk (NL)

(72) Inventors: Hans Dofferhoff, Reeuwijk (NL); Mike Dofferhoff, Reeuwijk (NL)

(73) Assignee: GREENWOOD INVESTMENTS B.V., Reeuwijk (NL)

( * ) Notice: Subject to any disclaimer, the term of this patent is extended or adjusted under 35 U.S.C. 154(b) by 0 days.

(21) Appl. No.: 17/562,726

(22) Filed: Dec. 27, 2021

(30) Foreign Application Priority Data

Oct. 5, 2021 (QZ) ..... PBR 20212497

(51) Int. Cl.
*A01H 6/48* (2018.01)
*A01H 5/02* (2018.01)

(52) U.S. Cl.
USPC ..... Plt./250

(58) Field of Classification Search
USPC ..... Plt./250
See application file for complete search history.

*Primary Examiner* — Annette H Para
(74) *Attorney, Agent, or Firm* — Penny J. Aguirre

(57) ABSTRACT

A new cultivar of *Hydrangea paniculata* plant named 'Bee Green' that is characterized by its inflorescences with sterile flower sepals that are light green in color that change to dark pink-red in color in autumn, its sturdy branches that do not lodge, its se panicles with firm sterile flowers, and its healthy foliage that has been observed to be disease and pest free.

2 Drawing Sheets

Botanical classification: *Hydrangea paniculata.*
Varietal denomination: 'Bee Green'.

CROSS-REFERENCE TO A RELATED APPLICATION

This application claims priority to European Community Plant Variety Office (CPVO) Plant Breeder's Rights Application No. 2021/2497 filed on Oct. 5, 2021 under 35 U.S.C. 119(f), the entire contents of which is incorporated by reference herein.

BACKGROUND OF THE INVENTION

The present invention relates to a new and distinct cultivar of *Hydrangea paniculata* and will be referred to hereafter by its cultivar name, 'Bee Green'. 'Bee Green' represents a new panicle *Hydrangea*, a perennial shrub grown for landscape use and as a potted plant.

'Bee Green' was discovered as a chance seedling in a production plot by the Inventors in Reeuwijk, The Netherlands in August of 2019. The parent plants are unknown.

Asexual propagation of the new cultivar was first accomplished by stem cuttings by one of the Inventors in October of 2019 in Reeuwijk, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bee Green' as a unique cultivar of *Hydrangea paniculata.*

1. 'Bee Green' exhibits inflorescences with sterile flower sepals that are light green in color that change to dark pink-red in color in autumn.
2. 'Bee Green' exhibits a sturdy branches that do not lodge.
3. 'Bee Green' exhibits dense panicles with firm sterile flowers.
4. 'Bee Green' exhibits healthy foliage that has been observed to be disease and pest free.

'Bee Green' can be most closely compared to the *Hydrangea paniculata* cultivars 'B2' (U.S. Plant Pat. No. 32,316) and 'Silver Dollar' (not patented). 'B2' differs from 'Bee Green' in having sterile flower sepals that are more white in color and leaves that are broader. 'Silver Dollar' differs from 'Bee Green' in having a larger inflorescences and sterile flower sepals that are more green in color.

BRIEF DESCRIPTION OF THE DRAWINGS

The accompanying color photographs illustrate the overall appearance and distinct characteristics of the new *Hydrangea*. The photographs were taken of a three-year-old plant of 'Bee Green' as field grown in Reeuwijk, The Netherlands and placed in a container for the photographs.

The photograph in FIG. 1 provides a side view of the plant habit of 'Bee Green' in bloom.

Figure 1:
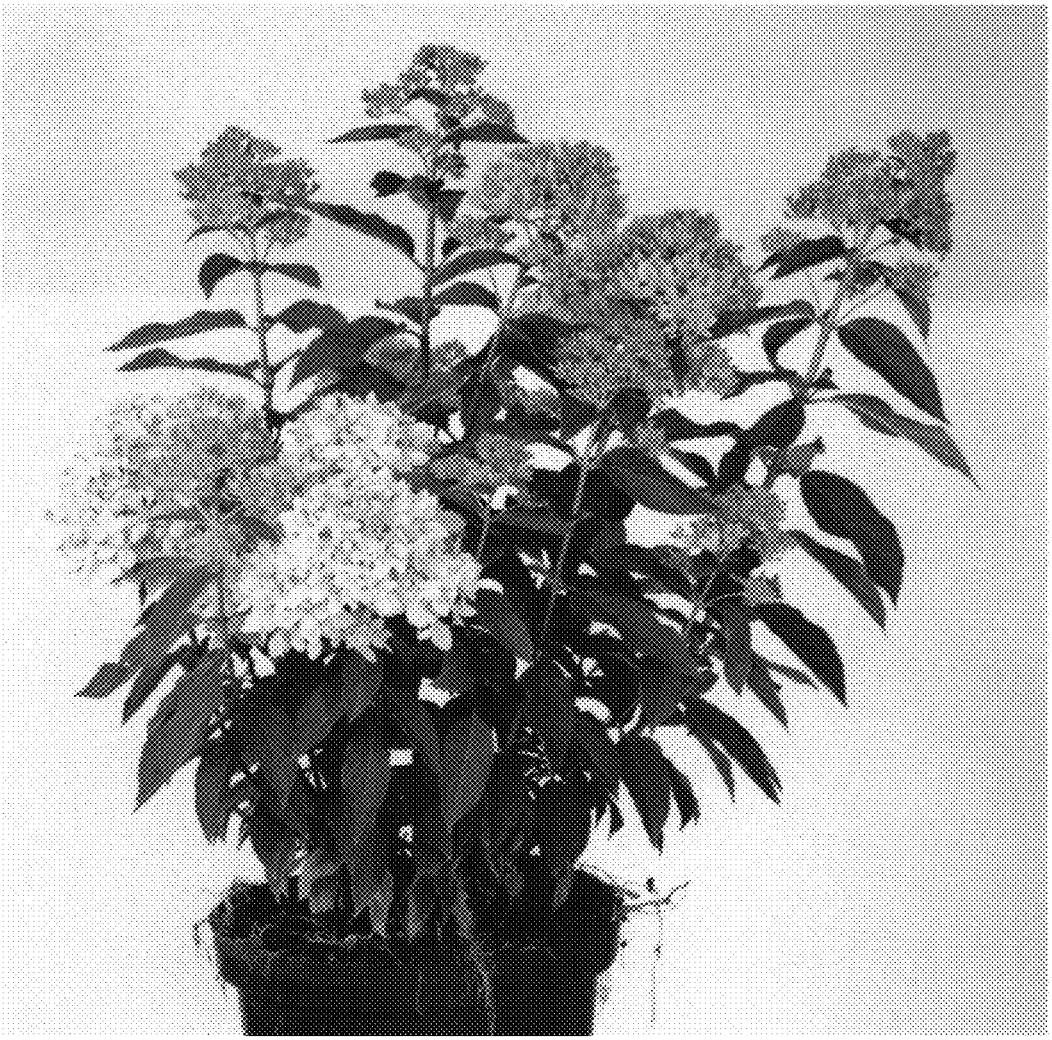
Figure 2:
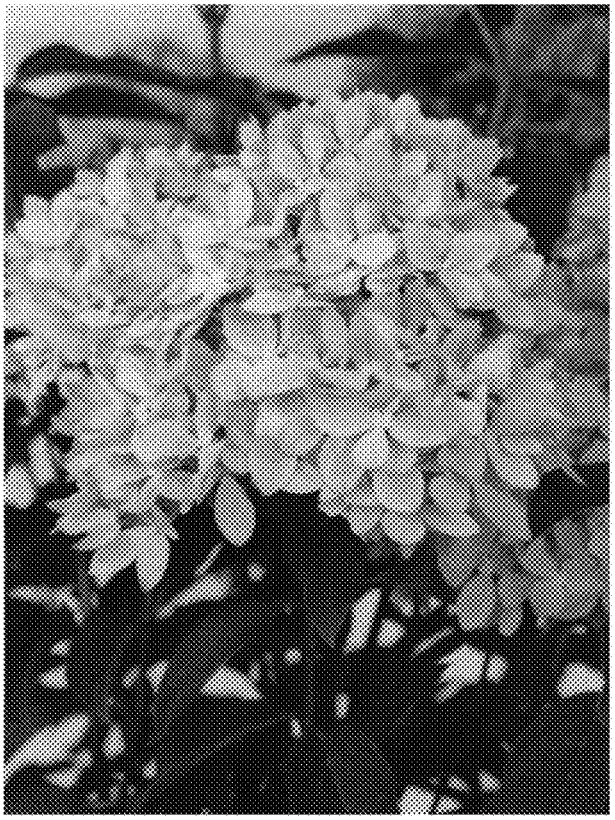

The photograph in FIG. 2 provides a close-up view of an inflorescence of 'Bee Green'.

Figure 3:
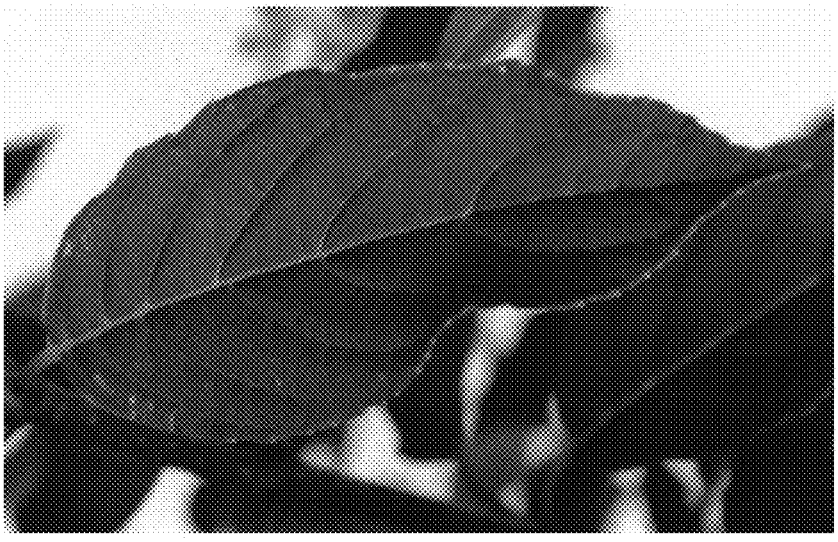

The photograph in FIG. 3 provides a close-up view of a leaf of 'Bee Green'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of three-year-old plants of 'Bee Green' as field grown in Reeuwijk, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Mid-summer to late summer in the Netherlands.

*Plant type*.—Herbaceous shrub.

*Plant habit*.—Broadly spreading, upright.

*Height and spread*.—Reaches 61.5 cm in height and 64.5 cm in spread in the landscape.

*Cold hardiness*.—At least in U.S.D.A. Zone 5.

*Diseases and pests*.—Plants have been observed to be disease and pest free, however no resistance to any particular agents has been identified.

*Root description*.—Fine, fibrous and dense, NN155A and 164A in color.

*Propagation*.—Stem cuttings.

*Root development*.—An average of 6 weeks for root initiation with a finished plant produced in about 12 months.

*Growth rate and vigor*.—Moderate.

Stem description:

*Stem shape*.—Rounded.

*Stem strength*.—Strong.

*Stem color*.—Young; 146B changing to 184A, mature; N199B and 200D, older bark a blend of 197A, 199A, 199B and N199A.

*Stem size*.—Average of 36.8 cm in length (excluding inflorescence) and 5.5 mm in diameter.

*Stem surface*.—Young stems are matte and densely covered with stiff hairs, average of 0.3 mm in length and match surface color, mature stems are matte and moderately covered with lenticels; an average of 1.25 mm in length and 0.75 mm in diameter, 164B to 164C in color.

*Stem aspect*.—Upright, average of 50° to soil level.

*Internode length*.—An average of 4.1 cm.

*Branching*.—Freely branching with an average of 21 lateral branches.

Foliage description:

*Leaf shape*.—Ovate to narrowly ovate.

*Leaf arrangement*.—Opposite or in whorls of 3.

*Leaf division*.—Simple.

*Leaf base*.—Near obtuse to short attenuate.

*Leaf apex*.—Apiculate to acute.

*Leaf margins*.—Shallowly finely serrate to slightly coarsely undulate.

*Leaf venation*.—Pinnate, color; upper and lower surface 146D.

*Leaf size*.—An average of 10.5 cm in length and 4.9 cm in width.

*Leaf attachment*.—Petiolate.

*Leaf number*.—An average of 18 per lateral stem.

*Leaf surface*.—Both surfaces; matte and slightly rugose, upper surface sparsely covered with short hairs, average of 0.4 mm in length, too small to measure color, lower surface very sparsely covered with very short hairs; an average of 0.3 mm in length and too small to measure color.

*Leaf color*.—Young upper surface; 143A, young lower surface 144A, mature upper surface; NN137B, mature lower surface; 146A.

*Petioles*.—An average of 1.9 cm in length and 2.5 mm in diameter, upper surface color 152A to 152B, margins 166B, lower surface color 152C, margined 166B, both surfaces slightly glossy, upper and lower surface sparsely covered with short hairs, average of 0.3 mm in length, too small to measure color.

Inflorescence description:

*Inflorescence type*.—Terminal conical panicle, comprised of sterile flowers above fertile flowers.

*Lastingness of inflorescence*.—Sterile flowers; persistent for an average of 6 weeks, fertile flowers; self-cleaning, an average of 5 days.

*Inflorescence number*.—One per lateral stem.

*Inflorescence size*.—An average of 15.1 cm in height and 15.8 cm in diameter.

*Flower number*.—An average of 280 sterile flowers and 115 fertile flowers per panicle.

*Flower fragrance*.—Medium strong, sweet and pleasant.

*Flower aspect*.—Sterile flowers; held upright to outward and slightly drooping, fertile flowers; held upright from peduncle.

*Flower size*.—Sterile flowers; up to 3.9 cm in diameter and 1.2 cm in depth, fertile flowers; an average of 1 cm in diameter and 6 mm in depth.

*Flower type*.—Sterile flowers rotate, fertile flowers rotate, dropped when mature.

*Flower buds*.—Sterile flowers; an average of 1 cm in length and 1.2 cm in diameter, cup-shaped, color; 144C, immature petals 157B, fertile flowers; an average of 4 mm in length, 3 mm in diameter, broad obovate in shape, color; 155C, immature petals 145D, immature ovary 148D.

*Petals*.—Sterile flowers; 4, rotate, ovate in shape, acute apex, entire margins, cuneate base, up to 3 mm in length and 1.2 mm in width, both surfaces; smooth, glabrous and slightly glossy, color when opening and fully open upper and lower surface NN155D, fertile flowers; 5, rotate in shape, ovate to moderately concave in shape, acute apex, cuneate base, entire margins, average of 3.5 mm in length and 1.5 mm in width, both surfaces glabrous and matte, color; upper and lower surface when opening and fully open NN155D.

*Peduncles*.—Strong, an average of 13.2 cm in length and 2.5 mm in width, 157A in color, surface is matte and moderately covered with thin pubescence an average of 0.5 mm in length and 157A in color.

*Pedicels*.—Sterile flowers; moderate strength, an average of 2.2 cm in length and 1 mm in width, 157A in color, surface is pubescent, held at a 40° angle, 145B to 145C in color, surface is matte and moderately covered with thin pubescence an average of 0.4 mm in length and matches surface color, fertile flowers; moderate strength, an average of 2 mm in length, 0.5 mm in diameter, held at a 20° angle, 145D and 157A in color, surface is very slightly glossy and glabrous.

*Sepals*.—Sterile flowers; 4 (occasionally 3), rotate, elliptic in shape, acute apex, cuneate base, entire margins, an average of 2.4 cm in length and 1.3 cm in width, both surfaces; glabrous and matte, color; upper surface when opening 145B, lower surface when opening 145C and 145D, upper surface when fully open 145A to 145B, margins 181D, fading to 145B, tinged with 179B and 180C, lower surface when fully open 145D, top 181D, fading to 145C, margins and top 180C and 180D, become 179B and 180C in autumn, fertile flowers; 5, rotate, deltoid in shape, acute apex, broad cuneate base, entire margins, 1.5 mm in length, 1 mm in width, both surfaces glabrous and matte, upper and lower surface when opening and fully open 145D in color.

*Bracts*.—None.

Reproductive organs:

*Gynoecium*.—Sterile flowers; occasionally a single deformed pistil is present, pistil; 1, 2 mm in length, stigma; club-shaped, 145C, style; 1.5 mm in length, 150D in color, no ovary present, fertile flowers; 3 pistils, occasionally 2, an average of 2 mm in length, stigma; club-shaped and 157D in color, style; 1 mm in length, 145D in color, ovary is 147D in color.

*Androecium*.—Sterile flowers; stamens; average of 8, filaments; 3 mm in length and NN155D in color, anthers; short, broadly oblong in shape, 0.5 mm in length, 161C in color, pollen; low in quantity, 156D in color, fertile flowers; stamens; average of 10, filaments; average of 4.5 mm in length, NN155D in color, anthers; short broad oblong in shape, 0.5 mm in length, 161C in color, pollen; low quantity, 156D in color.

*Fruit and seed*.—None observed to date.

It is claimed:

1. A new and distinct cultivar of *Hydrangea* plant named 'Bee Green' substantially as herein illustrated and described.

* * * * *